United States Patent
Murata et al.

(10) Patent No.: US 10,844,112 B2
(45) Date of Patent: Nov. 24, 2020

(54) METHOD FOR PURIFYING ANTIBODY OR ANTIBODY FRAGMENT CONTAINING κ-CHAIN VARIABLE REGION

(71) Applicant: KANEKA CORPORATION, Osaka (JP)

(72) Inventors: Dai Murata, Hyogo (JP); Shinichi Yoshida, Hyogo (JP); Kazunobu Minakuchi, Hyogo (JP)

(73) Assignee: KANEKA CORPORATION, Osaka (JP)

(*) Notice: Subject to any disclaimer, the term of this patent is extended or adjusted under 35 U.S.C. 154(b) by 0 days.

(21) Appl. No.: 16/183,308

(22) Filed: Nov. 7, 2018

(65) Prior Publication Data

US 2019/0211082 A1  Jul. 11, 2019

Related U.S. Application Data

(63) Continuation of application No. PCT/JP2017/016812, filed on Apr. 27, 2017.

(30) Foreign Application Priority Data

May 9, 2016 (JP) .................................. 2016-094178

(51) Int. Cl.

| C07K 16/06 | (2006.01) |
| C07K 16/00 | (2006.01) |
| C07K 16/12 | (2006.01) |
| B01D 15/38 | (2006.01) |
| C07K 1/22 | (2006.01) |
| C07K 1/36 | (2006.01) |

(52) U.S. Cl.
CPC ........ C07K 16/065 (2013.01); B01D 15/3804 (2013.01); C07K 1/22 (2013.01); C07K 1/36 (2013.01); C07K 16/00 (2013.01); C07K 16/1275 (2013.01); C07K 2317/515 (2013.01); C07K 2317/55 (2013.01); C07K 2317/622 (2013.01); C07K 2317/92 (2013.01)

(58) Field of Classification Search
None
See application file for complete search history.

(56) References Cited

U.S. PATENT DOCUMENTS

| 5,143,844 A | 9/1992 | Abrahmsen et al. |
| 5,965,390 A | 10/1999 | Bjorck et al. |
| 6,162,903 A | 12/2000 | Trowern et al. |
| 6,399,750 B1 | 6/2002 | Johansson |
| 6,831,161 B1 | 12/2004 | Uhlen et al. |
| 2002/0137918 A1 | 9/2002 | Gore et al. |
| 2003/0027283 A1 | 2/2003 | Bjorck et al. |
| 2003/0153735 A1 | 8/2003 | Breece et al. |
| 2005/0100970 A1 | 5/2005 | Uhlen et al. |
| 2005/0143566 A1 | 6/2005 | Hober |
| 2005/0215769 A1 | 9/2005 | Breece et al. |
| 2006/0134805 A1 | 6/2006 | Berg et al. |
| 2006/0142549 A1 | 6/2006 | Takeda et al. |
| 2006/0194950 A1 | 8/2006 | Hober et al. |
| 2006/0194955 A1 | 8/2006 | Hober et al. |
| 2007/0178541 A1 | 8/2007 | Pedersen et al. |
| 2007/0275873 A1 | 11/2007 | Heidner et al. |
| 2010/0022760 A1 | 1/2010 | Hober et al. |
| 2010/0286373 A1 | 11/2010 | Majima et al. |
| 2011/0112276 A1 | 5/2011 | Hober |
| 2011/0144311 A1 | 6/2011 | Chmielowski et al. |
| 2012/0238724 A1 | 9/2012 | Hober |
| 2013/0096276 A1 | 4/2013 | Yoshida et al. |
| 2013/0184438 A1 | 7/2013 | Hober et al. |
| 2013/0225796 A1 | 8/2013 | Takeda et al. |
| 2014/0018525 A1 | 1/2014 | Goklen et al. |
| 2014/0323695 A1 | 10/2014 | Takeda et al. |
| 2016/0024146 A1 | 1/2016 | Goklen et al. |
| 2016/0152668 A1 | 6/2016 | Hober |

(Continued)

FOREIGN PATENT DOCUMENTS

| CN | 1634990 A | 7/2005 |
| EP | 1123389 A1 | 8/2001 |

(Continued)

OTHER PUBLICATIONS

Hober, Sophia, et al., "Protein A chromatography for antibody purification"; Journal of Chromatography B, vol. 848 (2007); pp. 40-47 (8 pages).

Shukla, Abhinav A., et al., "Recent advances in large-scale production of monoclonal antibodies and related proteins"; Trends Biotechnol., vol. 28, No. 5 (2010); pp. 253-261 (9 pages).

Nelson, Aaron L., et al., "Development trends for therapeutic antibody fragments"; Nature Biotechnology, vol. 27, No. 4; Apr. 2009; pp. 331-337 (7 pages).

Bouvet, Jean-Pierre; "Immunoglobulin Fab Fragment-Binding Proteins"; Int. J. Immunopharmac., vol. 16, No. 5/6 (1994); pp. 419-424 (6 pages).

(Continued)

*Primary Examiner* — Daniel E Kolker
*Assistant Examiner* — James L Rogers
(74) *Attorney, Agent, or Firm* — Osha Bergman Watanabe & Burton LLP

(57) ABSTRACT

A method for purifying an antibody or an antibody fragment containing κ-chain variable region includes adsorbing at least one of the antibody or the antibody fragment onto an affinity separation matrix by contacting a liquid sample with the affinity separation matrix, washing the affinity separation matrix to remove impurities, and separating the at least one of the antibody or the antibody fragment from the affinity separation matrix by using an acetate buffer. The liquid sample includes the at least one of the antibody or the antibody fragment. The affinity separation matrix includes a water-insoluble carrier and a ligand selected from the group consisting of Protein L, a variant of Protein L, a domain of Protein L, and a variant of the domain. The ligand is immobilized on the water-insoluble carrier.

3 Claims, 6 Drawing Sheets

Specification includes a Sequence Listing.

(56) References Cited

U.S. PATENT DOCUMENTS

| | | |
|---|---|---|
| 2016/0237113 A1 | 8/2016 | Minakuchi |
| 2017/0159099 A1* | 6/2017 | Beam .................. C12Q 1/26 |
| 2017/0174721 A1 | 6/2017 | Goklen et al. |
| 2017/0320919 A1 | 11/2017 | Rodrigo et al. |
| 2017/0334947 A1 | 11/2017 | Murata et al. |
| 2018/0036445 A1 | 2/2018 | Monie et al. |
| 2019/0144511 A1 | 5/2019 | Rodrigo et al. |

FOREIGN PATENT DOCUMENTS

| | | | |
|---|---|---|---|
| EP | 3153581 A1 | 4/2017 | |
| JP | H07-506573 A | 7/1995 | |
| JP | H07507682 A | 8/1995 | |
| JP | 2006304633 A | 11/2006 | |
| JP | 2007252368 A | 10/2007 | |
| JP | 2008523140 A | 7/2008 | |
| JP | 2009/196998 A | 9/2009 | |
| JP | 2011/006489 A | 1/2011 | |
| JP | 2011-530606 A | 12/2011 | |
| JP | 2016079149 A | 5/2016 | |
| WO | 199717361 A1 | 5/1997 | |
| WO | 2000/015803 A1 | 3/2000 | |
| WO | 03080655 A1 | 10/2003 | |
| WO | 2005/033130 A2 | 4/2005 | |
| WO | 2005113584 A1 | 12/2005 | |
| WO | 2006126942 A1 | 11/2006 | |
| WO | WO-2007019376 A2 * | 2/2007 | ........... A61K 49/085 |
| WO | 2011/118699 A1 | 9/2011 | |
| WO | 2012/135415 A1 | 10/2012 | |
| WO | 2014/141150 A1 | 9/2014 | |
| WO | 2015041218 A1 | 3/2015 | |
| WO | 2015190457 A1 | 12/2015 | |
| WO | 2015190458 A1 | 12/2015 | |
| WO | 2016031902 A1 | 3/2016 | |
| WO | 2016121701 A1 | 8/2016 | |

OTHER PUBLICATIONS

Kastern, William, et al., "Structure of Peptostreptococcal Protein L and Identification of a Repeated Immunoglobulin Light Chain-binding Domain"; The Journal of Biological Chemistry, vol. 267, No. 18, Issue of Jun. 25, 1992; pp. 12820-12825 (6 pages).

Murphy, Jonathan P., et al., "The functional units of a peptostreptococcal protein L"; Molecular Microbiology, vol. 12, No. 6 (1994); pp. 911-920 (10 pages).

Housden, N.G., et al., "Immunoglobulin-binding domains: Protein L from Peptostreptococcus magnus"; Biochemical Society Transactions, vol. 31, Part 3 (2003); pp. 716-718 *(3 pages).

GE Healthcare Bio-Science AB, "Capto L"; Affinity chromatography; gelifesciences.com, Data file 29-0100-08 AC; (8 pages).

International Search Report dated Aug. 1, 2017, issued by the Japan Patent Office in corresponding International Application No. PCT/JP2017/016812 (2 pages).

R. Palmgren et al., "Improving the alkali stability of the kappa light chain-binding polypeptide from domain of peptostreptococcus protein L", Abstracts of Papers, 251st ACS National Meeting & Exposition, Mar. 13, 2016 (Abstract) (1 page).

B.M. Kihlberg et al., "Protein LG: A Hybrid Molecule with Unique Immunoglobulin Binding Properties", The Journal of Biological Chemistry, vol. 267, No. 35, Dec. 15, 1992, pp. 25583-25588 (6 pages).

H. G. Svensson et al., "Protein LA, a novel hybrid protein with unique single-chain Fv antibody- and Fab-binding properties", European Journal of Biochemistry, vol. 258, 1998, pp. 890-896 (7 pages).

M. Graille et al., "Complex between Peptostreptococcus magnus Protein L and a Human Antibody Reveals Structural Convergence in the Interaction Modes of Fab Binding Proteins", Structure, vol. 9, Aug. 2001, pp. 679-687 (9 pages).

S. P. Bottomley et al., "Cloning, expression and purification of Ppl-1, a kappa-chain binding protein, based upon protein L from Peptostreptococcus magnus", Bioseparation, vol. 5, 1995, pp. 359-367 (9 pages).

Capto (TM) L, Aug. 2014, [online] [retrieval date Apr. 11, 2016] <https://www.gelifesciences.com/gehcls_images/GELS/Related%20Content/Files/1346418936586/litdoc29010008_20141004004020.pdf> (8 pages).

N. G. Housden et al., "Observation and Characterization of the Interaction between a Single Immunoglobulin Binding Domain of Protein L and Two Equivalents of Human k Light Chains," The Journal of Biological Chemistry, vol. 279, No. 10, Mar. 5, 2004, pp. 9370-9378 (9 pages).

X. Tadeo et al., "Protein Stabilization and the Hofmeister Effect: The Role of Hydrophobic Solvation," Biophysical Journal, vol. 97, Nov. 2009, pp. 2595-2603 (9 pages).

A. V. Glyakina et al., "Mechanical stability analysis of the protein L immunoglobulin-binding domain by full alanine screening using molecular dynamics simulations", Biotechnology Journal, 2015, vol. 10, pp. 386-394 (11 pages).

H. G. Svensson et al., "Contributions of Amino Acid Side Chains to the Kinetics and Thermodynamics of the Bivalent Binding of Protein L to Ig k Light Chain", Biochemistry, 2004, vol. 43, pp. 2445-2457 (13 pages).

O. Millet et al., "The Effects of Mutations on Motions of Side-chains in Protein L Studied by 2H NMR Dynamics and Scalar Couplings", J. Mol. Biol., 2003, vol. 329, pp. 551-563 (13 pages).

J. A. Beckingham et al., "Interactions between a single immunoglobulin-binding domain of protein L from Peptostreptococcus magnus and a human k light chain", Biochem. J., 1999, vol. 340, pp. 193-199 (7 pages).

S. Yoshida et al., "Rational design and engineering of protein A to obtain the controlled elution profile in monoclonal antibody purification", Chem-Bio Informatics Journal, vol. 12, 2012, pp. 1-13 (13 pages).

D. E. Kim et al. "A Breakdown of Symmetry in the Folding Transition State of Protein L", Journal of Molecular Biology, 2000, vol. 298, No. 5, pp. 971-984 (14 pages).

X Yang et al. "Total chemical synthesis of the B1 domain of protein L from Peptostreptococcus magnus", Bioorganic Chemistry 2006, vol. 34, No. 3, pp. 131-141 (11 pages).

M. Kastner, "Protein liquid chromatography," Journal of Chromatography Library, vol. 61, section 22.5.2, p. 811, 2000 (3 pages).

Office Action issued in U.S. Appl. No. 16/176,090; dated Oct. 1, 2019 (14 pages).

International Search Report issued in International Application No. PCT/JP2017/016819, dated Jul. 25, 2017 (2 pages).

A. Murray et al, "Epitope Affinity Chromatography and Biophysical Studies of Monoclonal Antibodies and Recombinant Antibody Fragments", Journal of Chromatographic Science; vol. 40, Jul. 2002; pp. 343-349 (7 pages).

B. R. Hubbard et al, "Vitamin K-dependent carboxylase: Affinity purification from bovine liver by using a synthetic propeptide containing the Y-carboxylation recognition site", Proceedings of the National Academy of Sciences of the Jnited States of America; vol. 86, Sep. 1989; pp. 6893-6897 (6 pages).

* cited by examiner

METHOD FOR PURIFYING ANTIBODY OR ANTIBODY FRAGMENT CONTAINING κ-CHAIN VARIABLE REGION

TECHNICAL FIELD

One or more embodiments of the present invention relate to a method for successfully purifying an antibody or an antibody fragment containing κ-chain variable region without giving damage to the antibody or the antibody fragment.

BACKGROUND

As one of important functions of a protein, a capability to specifically bind to a specific molecule is exemplified. The function plays an important role in an immunoreaction and signal transduction in a living body. A technology utilizing the function for purifying a useful substance has been actively developed. As one example of proteins which are actually utilized industrially, for example, Protein A affinity separation matrix has been used for capturing an antibody drug to be purified with high purity at one time from a culture of an animal cell (Non-patent documents 1 and 2). Hereinafter, Protein A is abbreviated as "SpA" in some cases.

In order to purify an antibody by using an affinity separation matrix, in general, the antibody is selectively bound to a ligand of the affinity separation matrix, the affinity separation matrix is washed to remove an impurity, and then the antibody is separated from the affinity separation matrix. For example, Patent document 1 discloses a method for reducing an aggregation of an antibody by collecting a monomeric monoclonal antibody fraction from SpA affinity chromatography column to form a Protein A product pool, and adjusting a pH value of the product pool to about 3.5-about 4.5. As a buffer to elute an antibody, citrate and acetate are exemplified. In addition, it is described in Patent documents 2 and 3 to use an aqueous solution of a citrate salt or an acetate salt as a washing liquid to wash SpA on which an antibody is adsorbed, though the aqueous solution is not used for eluting the antibody.

An antibody drug which has been developed is mainly a monoclonal antibody, and a monoclonal antibody has been produced on a large scale by using recombinant cell cultivation technology. A "monoclonal antibody" means an antibody obtained from a clone derived from a single antibody-producing cell. Most of antibody drugs which are presently launched are classified into an immunoglobulin G (IgG) subclass in terms of a molecular structure. In addition, an antibody drug consisting of an antibody fragment has been actively subjected to clinical development. An antibody fragment is an antibody derivative having a molecular structure obtained by fragmenting an immunoglobulin, and various antibody fragment drugs have been clinically developed (Non-patent Document 3).

In an initial purification step of an antibody drug production, the above-described SpA affinity separation matrix is utilized. SpA is, however, basically a protein which specifically binds to a Fc region of IgG. Thus, SpA affinity separation matrix cannot capture an antibody fragment which does not contain a Fc region. Accordingly, an affinity separation matrix capable of capturing an antibody fragment which does not contain a Fc region of IgG is highly required industrially in terms of a platform process for purifying an antibody drug.

A plurality of peptides which can bind to a region except for a Fc region of IgG have been already known (Non-patent Document 4). Among such peptides, a peptide which can bind to a variable region as an antibody-binding domain may be most preferred in terms of many kinds of antibody fragment format to be bound and an ability to bind to IgM and IgA. As such a peptide, for example, Protein L has been well-known. Hereinafter, Protein L is abbreviated as "PpL" in some cases. PpL is a protein which contains a plurality of κ-chain variable region-binding domains, and amino acid sequences of each κ-chain variable region-binding domain are different from each other. Hereinafter, κ-chain variable region is abbreviated as "VL-κ" in some cases. In addition, the number of VL-κ-binding domains and amino acid sequences of each VL-κ-binding domain are different depending on the kind of strain. For example, the number of VL-K-binding domains in PpL of *Peptostreptococcus magnus* 312 strain is 5, and the number of VL-κ-binding domains in PpL of *Peptostreptococcus magnus* 3316 strain is 4 (Non-patent documents 5 to 7, and Patent documents 4 and 5). There are no domains that have the same amino acid sequence as each other in the totally 9 VL-κ-binding domains.

PATENT DOCUMENT

Patent Document 1: JP 2011-530606 T
Patent Document 2: JP 2009-196998 A
Patent Document 3: JP 2011-6489 A
Patent Document 4: JP H7-506573 T
Patent Document 5: JP H7-507682 T

Non-Patent Document

Non-patent Document 1: Hober S., et al., J. Chromatogr. B, 2007, vol. 848, pp. 40-47
Non-patent Document 2: Shukla A. A., et al., Trends Biotechnol., 2010, vol. 28, pp. 253-261
Non-patent Document 3: Nelson A. N., et al., Nat. Biotechnol., 2009, vol. 27, pp. 331-337
Non-patent Document 4: Bouvet P. J., Int. J. Immunopharmac., 1994, vol. 16, pp. 419-424
Non-patent Document 5: Kastern W., et al., J. Biol. Chem., 1992, vol. 267, pp. 12820-12825
Non-patent Document 6: Murphy J. P., et al., Mol. Microbiol., 1994, vol. 12, pp. 911-920
Non-patent Document 7: Housden N. G., et al., Biochemical Society Transactions, 2003, vol. 31, pp. 716-718

As described above, with respect to the purification of an antibody by using an affinity separation matrix containing SpA, a ligand and an elution condition have been sufficiently studied. On the one hand, with respect to an affinity separation matrix containing PpL, it is hard to say that sufficient study has been made.

For example, in the case of an affinity separation matrix containing SpA, it has been studied to elute an antibody in the condition of relatively high pH. On the one hand, in the case of an affinity separation matrix containing PpL, a sufficient study has not been made, and an antibody or a VL-κ-containing antibody fragment may undergo a chemical change, be cleaved or be easily agglutinated due to an eluate having low pH. In addition, when an antibody or an antibody fragment is separated from an affinity separation matrix, if an elution peak is not sharp, not only a purity is decreased due to overlapped peaks but also it requires time and effort to purify, concentrate and dry the antibody and antibody fragment from a solution of elution fractions since a solution amount of the elution pool is increased.

SUMMARY

One or more embodiments of the present invention provide a method for successfully purifying an antibody or an antibody fragment containing κ-chain variable region with a sharp elution peak and without giving a damage to the antibody or antibody fragment containing κ-chain variable region, since a pH value of an eluate can be adjusted to relatively higher.

The present inventors completed one or more embodiments of the present invention by finding that an antibody or an antibody fragment containing κ-chain variable region can be successfully purified with a sharp elution peak, even if a pH value of an eluate is adjusted to relatively higher, by using an acetate buffer as the eluate for purifying the antibody and antibody fragment with using an affinity separation matrix containing PpL.

Hereinafter, one or more embodiments of the present invention are described.

[1] A method for purifying an antibody or an antibody fragment containing κ-chain variable region, comprising the steps of:

contacting a liquid sample containing at least one of the antibody and the antibody fragment with an affinity separation matrix in order to adsorb the antibody and/or the antibody fragment on the affinity separation matrix, wherein Protein L, a domain of Protein L, a variant of Protein L, or a variant of a domain of Protein L is immobilized as a ligand on a water-insoluble carrier in the affinity separation matrix, washing the affinity separation matrix to remove an impurity other than the antibody and/or the antibody fragment, and separating the antibody and/or the antibody fragment on the affinity separation matrix from the affinity separation matrix by using an acetate buffer.

[2] The method according to the above [1], wherein a pH value of the acetate buffer is 2.5 or higher and 4.0 or lower.

[3] The method according to the above [1] or [2], wherein a concentration of an acetate ion in the acetate buffer is 10 mM or more and 500 mM or less.

[4] The method according to any one of the above [1] to [3], wherein a temperature in contacting the liquid sample with the affinity separation matrix is 4° C. or higher and 40° C. or lower.

[5] The method according to any one of the above [1] to [4], wherein a temperature in separating the antibody and/or the antibody fragment from the affinity separation matrix is 4° C. or higher and 40° C. or lower.

According to one or more embodiments of the present invention, when an antibody or a VL-κ-containing peptide is separated from an affinity separation matrix containing PpL, a damage to the antibody or antibody fragment can be reduced, since a pH value of an eluate can be adjusted to relatively higher. In addition, the above antibody and antibody fragment can be easily further purified, concentrated and dried from an elution pool, since an elution peak of the antibody or antibody fragment is sharp and an amount of the elution pool is reduced. As a result, a cost to purify an antibody or a VL-K-containing antibody fragment can be cut.

DETAILED DESCRIPTION OF THE EMBODIMENTS

Figure 1:
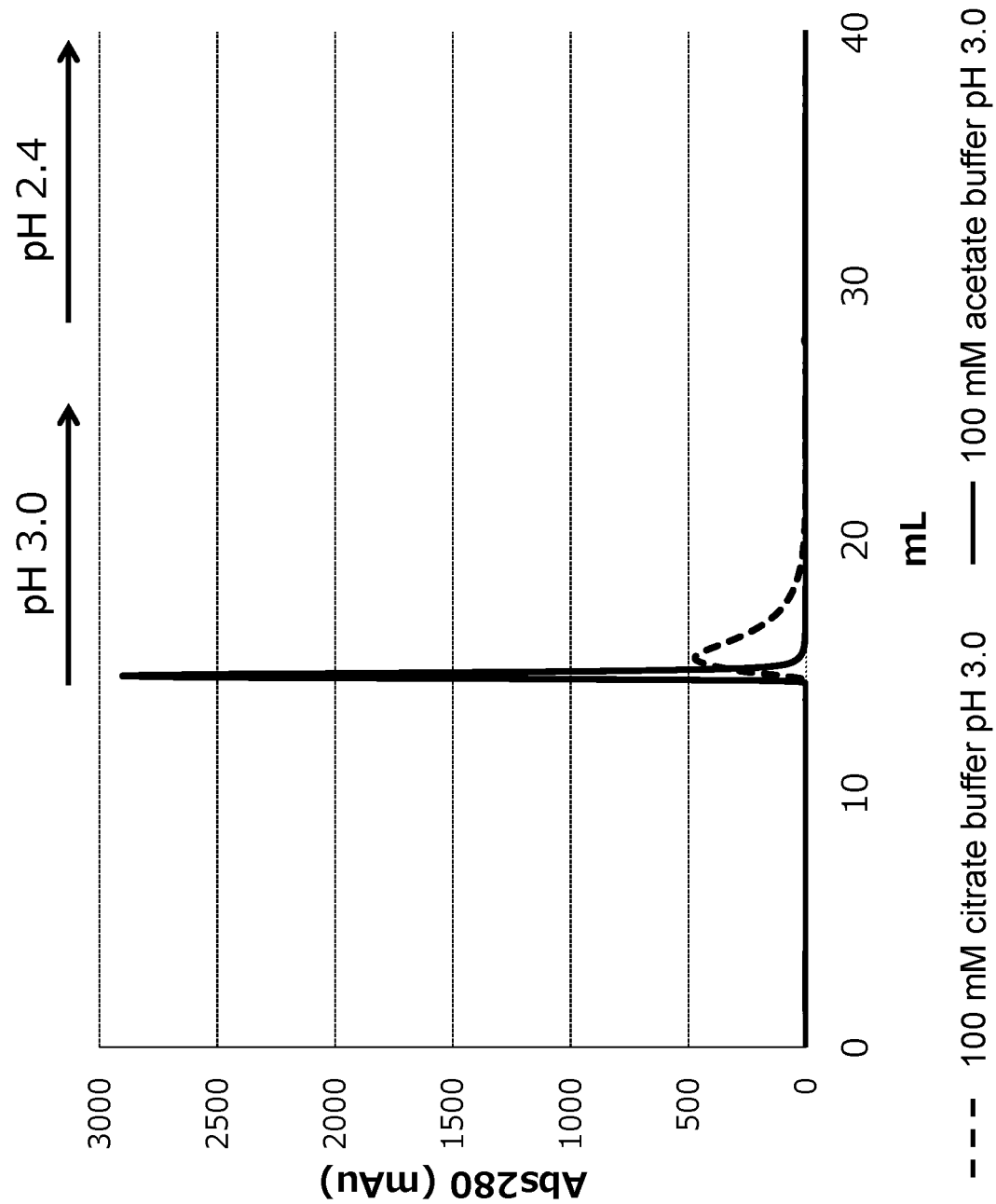
FIG. 1 represents an elution profile in the case where an acetate buffer or a citrate buffer having pH of 3.0 was used as an eluate, when a Fab fragment containing VL-K was purified by using a commercially available affinity separation matrix on which Protein L was immobilized. A citrate buffer having pH of 2.4 was also used in order to dissociate a Fab fragment remaining in the matrix.

One or more embodiments relate to a method for successfully purifying an antibody and an antibody fragment which contain VL-κ without giving a damage to the antibody and antibody fragment by using an affinity separation matrix on which Protein L, a domain of Protein L, a variant of Protein L, or a variant of a domain of Protein L is immobilized. Hereinafter, each step according to one or more embodiments of the present invention is described.

Step 1: Adsorption Step

In the present step, a liquid sample containing at least one of an antibody and a VL-κ-containing antibody fragment is contacted with an affinity separation matrix in which Protein L, a domain of Protein L, a variant of Protein L, or a variant of a domain of Protein L is immobilized as a ligand on a water-insoluble carrier, in order to adsorb the antibody and/or antibody fragment on the affinity separation matrix.

An "immunoglobulin (Ig)" is a glycoprotein produced by a B cell of a lymphocyte and has a function to recognize a specific molecule such as a protein to be bound. An immunoglobulin has not only a function to specifically bind to a specific molecule referred to as antigen but also a function to detoxify and remove an antigen-containing factor in cooperation with other biological molecule or cell. An immunoglobulin is generally referred to as "antibody", and the name is inspired by such functions.

All of immunoglobulins basically have the same molecular structure. The basic structure of an immunoglobulin is a Y-shaped four-chain structure. The four-chain structure is composed of two light chains and two heavy chains of polypeptide chains. A light chain (L chain) is classified into two types of λchain and κ chain, and all of immunoglobulins have either of the chains. A heavy chain (H chain) is classified into five types of γchain, μ chain, α chain, δ chain and εchain, and an immunoglobulin is classified into isotypes depending on the kind of a heavy chain. An immunoglobulin G (IgG) is a monomer immunoglobulin, is composed of two γchains and two light chains, and has two antigen-binding sites.

A lower half vertical part in the "Y" shape of an immunoglobulin is referred to as a "Fc region", and an upper half "V" shaped part is referred to as a "Fab region". A Fc region has an effector function to initiate a reaction after an antibody binds to an antigen, and a Fab region has a function to bind to an antigen. A Fab region of a heavy chain and a Fc region are bound to each other through a hinge part. Papain, which is a proteolytic enzyme and which is contained in *papaya*, decomposes a hinge part to cut into two Fab regions and one Fc region. The domain part close to the tip of the "Y" shape in a Fab region is referred to as a "variable region (V region)", since there are various changes of the amino acid sequence in order to bind to various antigens. A variable region of a light chain is referred to as a "VL region", and a variable region of a heavy chain is referred to as a "VH region". A Fab region except for a V region and a Fc region are referred to as a "constant region (C region)", since there is relatively less change. A constant region of a light chain is referred to as a "CL region", and a constant region of a heavy chain is referred to as a "CH region". A CH region is further classified into three regions of CH1 to CH3. A Fab region of a heavy chain is composed of a VH region and CH1, and a Fc region of a heavy chain is composed of CH2 and CH3. There is a hinge part between CH1 and CH2. PpL binds to a variable region of which light chain is κ chain (VL-κ) (Non-patent Documents 5 to 7).

The ligand of the affinity separation matrix according to one or more embodiments of the present invention is based on the sequence of Protein L (PpL) and binds to a κ chain variable region (VL-κ) of an immunoglobulin. The antibody to which an affinity separation matrix according to one or more embodiments of the present invention binds may be any antibody containing VL-κ, and may be IgG containing a Fab region and a Fc region without deficiency, other Ig class such as IgM, IgD and IgA, or a derivative of an immunoglobulin molecule prepared by a protein engineering alteration. The antibody fragment to which the affinity separation matrix used by one or more embodiments of the present invention binds is not particularly restricted as long as the antibody fragment contains VL-κ. For example, the antibody fragment is exemplified by a Fab fragment prepared by fragmenting immunoglobulin G into a Fab region only, scFv and diabody consisting of a variable region of immunoglobulin G, chimeric immunoglobulin G prepared by replacing a part of human immunoglobulin G domains with an immunoglobulin G domain of other organism to be fused, immunoglobulin G of which sugar chain in the Fc region is altered, and a scFv fragment to which a drug is covalently bonded.

The above-described liquid sample is not particularly restricted as long as the liquid sample contains at least one of an antibody and a VL-κ-containing antibody fragment to be purified, and in one or more embodiments, it is preferred that the liquid sample is a solution in which an antibody and/or a VL-κ-containing antibody fragment is dissolved in water. Such a liquid sample is exemplified by a serum sample which contains an antibody and/or a VL-κ-containing antibody fragment, a culture medium or a homogenate supernatant of a bacterium and a fungus which culture medium and supernatant contain a VL-κ-containing antibody fragment, and a homogenate of a hybridoma which produces a monoclonal antibody. In one or more embodiments, it is preferred that the liquid sample is approximately neutral and the pH value thereof is 6 or more and 8 or less. The solvent of the liquid sample may be water only, may contain a water-miscible organic solvent such as $C_1$-4 alcohol as long as the liquid sample contains water as a main component, and may be a buffer solution of which pH is 6 or more and 8 or less.

In the affinity separation matrix used in one or more embodiments of the present invention, Protein L, a domain of Protein L, a variant of Protein L, or a variant of a domain of Protein L is immobilized as a ligand on a water-insoluble carrier. Hereinafter, the Protein L, domain of Protein L, variant of Protein L, or variant of a domain of Protein L is collectively referred to as "VL-κ-binding peptide" in some cases.

The term "peptide" in one or more embodiments of the present invention means any molecules having a polypeptide structure. In the range of the "peptide", not only a so-called protein but also a fragmented peptide and a peptide to which other peptide is bound through a peptide bond are included. The term "domain" means a unit of higher-order structure of a protein. A domain is composed of from dozens to hundreds of amino acid residues, and means a peptide unit which can sufficiently serve some kind of a physicochemical or biochemical function. The term "domain of Protein L" in one or more embodiments of the present invention has an affinity for VL-κ. The term "variant" of Protein L and a domain means a protein or peptide obtained by introducing at least one substitution, addition or deletion of an amino acid into a sequence of a wild Protein L and a domain thereof. The affinity of the variant for VL-κ may be at least maintained and preferably improved. The number of the variation may be preferably 10 or less, and more preferably 5 or less.

The "Protein L" (PpL) is a protein derived from a cell wall of anaerobic gram-positive coccus in the genus of *Peptostreptococcus*. PpL may be preferably derived from *Peptostreptococcus magnus*, and preferably 2 kinds of PpLs derived from *Peptostreptococcus magnus* 312 strain and *Peptostreptococcus magnus* 3316 strain, but is not restricted thereto (Non-patent documents 4 to 6).

PpL contains a plurality of VL-κ-binding domains having 70 to 80 residues in the protein molecule. The number of VL-κ-binding domains contained in PpL 312 is 5, and the number of VL-κ-binding domains contained in PpL 3316 is 4. The VL-κ-binding domains contained in PpL 312 are referred to as B1 to 5 domains in the order from the N-terminal, and the VL-κ-binding domains contained in PpL 3316 are referred to as C 1 to 4 domains in the order from the N-terminal (Non-patent documents 5 and 6).

It is clarified from the research that about 20 resides in the VL-κ-binding domain of PpL at the N-terminal do not form a specific secondary structure, and even if the N-terminal is deleted, the three-dimensional structure of the VL-κ-binding domain is maintained and the VL-κ-binding ability is shown (Non-patent document 7).

As described above, PpL is a protein in which 4 or 5 VL-κ-binding domains are linked in tandem. The VL-κ-binding peptide according to one or more embodiments of the present invention, therefore, may be a monomer or a multimer composed of 2 or more, preferably 3 or more, even more preferably 4 or more, and even more preferably 5 or more linked VL-κ-binding peptides as a monodomain. With respect to the upper limit of the number of the domains to be linked, 10 or less may be exemplified, 8 or less may be preferred, and 6 or less may be more preferred. The multimer may be a homomultimer in which one kind of VL-κ-binding peptides are linked, such as homodimer and homotrimer, or a heteromultimer in which two or more kinds of VL-κ-binding peptides are linked, such as heterodimer and heterotrimer.

In the above-described multimer, a method for connecting the monomers of VL-κ-binding peptide is exemplified by a connecting method through one or more amino acid residues, but is not restricted thereto. The number of the amino acid residue for connection is not particularly restricted, and may be preferably 20 residues or less, and more preferably 15 residues or less. In one or more embodiments, it is preferred to utilize the sequence which connects B1 and B2, B2 and B3, B3 and B4, B4 and B5, C1 and C2, C2 and C3, or C3 and C4 in wild PpL. From another perspective, it may be preferred that the amino acid residue for connection does not destabilize a three dimensional structure of the monomer of VL-κ-binding peptide.

As an example of the embodiments, a fusion peptide characterized in that VL-κ-binding peptide or a multimer formed by connecting two or more VL-κ-binding domains as one component is fused with other peptide having a different function is exemplified as the ligand of the affinity separation matrix according to one or more embodiments of the present invention. Such a fusion peptide is exemplified by a peptide fused with albumin or GST, i.e. glutathione S-transferase, but is not restricted to the examples. In addition, peptides fused with a nucleic acid such as DNA aptamer, a drug such as an antibiotic or a polymer such as PEG, i.e. polyethylene glycol, are also included in one or more embodiments of the present invention as long as the availability of the affinity separation matrix according to one or more embodiments of the present invention is utilized in such a fusion peptide.

The VL-κ-binding peptide used in one or more embodiments of the present invention can be prepared by an ordinary method. Specifically, the DNA which encodes an amino acid sequence of the desired VL-κ-binding peptide or a fragment thereof is chemically synthesized, the DNA encoding the VL-κ-binding peptide is amplified by PCR, and the DNA is incorporated into a vector. *Escherichia coli* or the like is infected with the obtained vector and cultivated. The VL-κ-binding peptide may be purified from the cultivated bacterial body or the culture medium by chromatography or the like.

The affinity separation matrix used in one or more embodiments of the present invention is prepared by immobilizing the above-described VL-κ-binding peptide on a water-insoluble carrier. The "water-insoluble carrier" used in one or more embodiments of the present invention shows insolubility to an aqueous solvent which is a solvent of the liquid sample containing VL-κ-binding peptide, and when a ligand is immobilized on the water-insoluble carrier, the antibody and antibody fragment which specifically binds to the ligand can be purified. The water-insoluble carrier usable in one or more embodiments of the present invention is exemplified by an inorganic carrier such as glass beads and silica gel; an organic carrier composed of a synthetic polymer such as cross-linked polyvinyl alcohol, cross-linked polyacrylate, cross-linked polyacrylamide and cross-linked polystyrene; an organic carrier composed of a polysaccharide such as crystalline cellulose, cross-linked cellulose, cross-linked agarose and cross-linked dextran; and a composite carrier obtained by the combination of the above carriers, such as an organic-organic composite carrier and an organic-inorganic composite carrier. The commercially available product thereof is exemplified by porous cellulose gel GCL2000, Sephacryl S-1000 prepared by crosslinking allyl dextran and methylene bisacrylamide through a covalent bond, an acrylate carrier Toyopearl, a cross-linked agarose carrier Sepharose CL4B, and a cross-linked cellulose carrier Cellufine. It should be noted, however, that the water-insoluble carrier usable in one or more embodiments of the present invention is not restricted to the carriers exemplified as the above.

In one or more embodiments, it is preferred that the water-insoluble carrier usable in one or more embodiments of the present invention has large surface area and is porous with a large number of fine pores having a suitable size in terms of a purpose and a method of using the affinity separation matrix. The carrier may have any form such as beads, monolith, fiber and membrane including hollow fiber, and any form can be selected.

As a method for immobilizing the VL-κ-binding peptide as the ligand in one or more embodiments of the present invention on a water-insoluble carrier, an ordinary method may be used. For example, the ligand is immobilized by using a reactive group on the surface of a water-insoluble carrier. Specifically, there is a reactive group such as an amino group, a hydroxy group and a carboxy group on the surface of a general water-insoluble carrier. The reactive group may be activated or substituted by other reactive group, or a linker group having a reactive group may be introduced on the reactive group. For example, when an epoxy group is introduced on the surface of a water-insoluble carrier by using epichlorohydrin, diglycidyl ether, 1,4-bis(2,3-epoxypropoxy)butane or the like, or when an iodoacetyl group, a bromoacetyl group, a maleimide group, a N-hydroxysuccinimide or the like is introduced on the surface of a water-insoluble carrier, a coupling reaction between the VL-κ-binding peptide and the reactive group can be easily accelerated.

When a linker group is used for immobilizing the ligand on a water-insoluble carrier, the linker group is not particularly restricted. The linker group is exemplified by a $C_{1-6}$ alkylene group, an amino group (—NH—), an imino group (>C=N— or —N=C<), an ether group (—O—), a thioether group (—S—), a carbonyl group (—C(=O)—), a thionyl group (—C(=S)—), an ester group (—C(=O)—O— or —O—C(=O)—), an amide group (—C(=O)—NH— or —NH—C(=O)—), a sulfoxide group (—S(=O)—), a sulfonyl group (—S(=O)$_2$—), a sulfonylamide group (—NH—S(=O)$_2$— and —S(=O)$_2$—NH—), and a group formed by binding a plurality of the above-described groups. When the linker group is formed by binding a plurality of the above-described groups, the number of the bound groups may be preferably not more than 10 or not more than 5, and more preferably 3 or less.

A spacer molecule composed of a plurality of atoms may be introduced between the ligand and carrier. Alternatively, the ligand may be directly immobilized on the carrier. In addition, the VL-κ-binding peptide according to one or more embodiments of the present invention may be chemically modified for immobilization.

In the present step, the above-described liquid sample is contacted with the above-described affinity separation matrix in order to selectively bind an antibody and/or an antibody containing VL-κ with the above-described VL-κ- binding peptide as a ligand. The specific condition for the contact is not particularly restricted, and the above-described liquid sample and the above-described affinity separation matrix may be simply mixed. Alternatively, for example, in terms of convenience, it may be preferred that a column is filled with the affinity separation matrix according to one or more embodiments of the present invention to be an affinity column and the liquid sample is flown through the affinity column to selectively adsorb the above-described antibody and/or antibody fragment on the VL-κ-binding peptide.

The condition of the present step may be appropriately adjusted as long as the above-described antibody and/or antibody fragment contained in the above-described liquid sample is sufficiently adsorbed on the above-described affinity separation matrix. For example, the temperature of the present step may be adjusted to 4° C. or higher and 40° C. or lower. When the temperature is 4° C. or higher, the above-described liquid sample may not be frozen and the liquid sample having appropriate flowability may be flown through the matrix. On the one hand, when the temperature is 40° C. or lower, the above-described antibody and/or antibody fragment contained in the above-described liquid sample may be purified in a state where the possibility of the antibody and/or antibody fragment is thermally denatured is low. When a chromatography system is used, the temperature can be easily adjusted by using a column jacket or the like.

Step 2: Step for Washing Affinity Separation Matrix

In the present step, the affinity separation matrix on which the above-described antibody and/or antibody fragment is adsorbed is washed to remove an impurity other than the above-described antibody and/or antibody fragment. Even after the present step, the above-described antibody and/or antibody fragment is adsorbed on the affinity separation matrix.

As a washing liquid usable for washing the affinity separation matrix in the present step, a washing liquid which does not disturb interaction between the above-described antibody and/or antibody fragment and the VL-κ-binding peptide is used. For example, water and a buffer of which pH is 6 or more and 8 or less can be used as the washing liquid. An amount of the washing liquid to be used may be appropriately adjusted within the range where an impurity can be sufficiently removed from the affinity separation matrix. For example, when a chromatography system is used, it can be easily determined by monitoring an elution profile whether an impurity can be sufficiently removed or not.

Step 3: Step for Separating Antibody and/or Antibody Fragment

In one or more embodiments of the present invention, the above-described antibody and/or antibody fragment is separated from the affinity separation matrix on which the antibody and/or antibody fragment is adsorbed by using an acetate buffer as an eluate. By the present step, the purified antibody and/or antibody fragment can be obtained.

In one or more embodiments of the present invention, an acetate buffer is used as the eluate for eluting the antibody and/or antibody fragment containing VL-κ. The antibody and/or antibody fragment can be efficiently eluted and a damage of the antibody and/or antibody fragment can be reduced due to the eluate by using the acetate buffer a damage, even if the pH of the acetate buffer is relatively high. In addition, by using an acetate buffer as an eluate, the antibody and/or antibody fragment can be successfully dissociated from the VL-K-binding peptide. For example, when a column is used, an elution peak of the antibody and/or antibody fragment becomes sharp. As a result, a solution amount of a fraction containing the antibody and/or antibody fragment can be reduced, and it becomes easy to further purify and dry the antibody and/or antibody fragment.

An acetate buffer can be obtained by, for example, mixing an aqueous solution of a salt of acetic acid and a weak base, such as a sodium acetate aqueous solution, with an acetic acid aqueous solution in a proportion to adjust the pH as intended. The pH of the acetate buffer may be preferably 2.5 or higher and 4.0 or lower. When the pH is 2.5 or higher, the chemical change or the like of the antibody and/or antibody fragment can be suppressed more surely. On the one hand, when the pH is 4.0 or lower, the antibody and/or antibody fragment can be eluted more surely. The pH may be more preferably 2.8 or higher, even more preferably 3.0 or higher, and more preferably 3.8 or lower, even more preferably 3.5 or lower.

An ion concentration of the acetate buffer may also effect on the elution of the antibody and/or antibody fragment. For example, the acetate ion concentration of the acetate buffer may be preferably 10 mM or more and 500 mM or less. When the acetate ion concentration is 10 mM or more, the elution peak of the antibody and/or antibody fragment may become sharp more easily. On the one hand, when the acetate ion concentration is 500 mM or less, it may become easier to adjust the pH of the obtained elution fragment of the antibody and/or antibody fragment. The acetate ion concentration may be more preferably 50 mM or more, even more preferably 80 mM or more, and more preferably not more than 400 mM or not more than 300 mM, even more preferably 200 mM or less, particularly preferably 150 mM or less.

The condition of the present step may be appropriately adjusted within the range where the antibody and/or antibody fragment which is adsorbed on the affinity separation matrix is sufficiently separated to be eluted. For example, the temperature of the present step may be adjusted to 4° C. or higher and 40° C. or lower. When the temperature is 4° C. or higher, the eluate or the like may not be frozen and the eluate having appropriate flowability may be flown through the matrix. On the one hand, when the temperature is 40° C. or lower, the above-described antibody and/or antibody fragment may be eluted in a state where the possibility that the antibody and/or antibody fragment is thermally denatured is low.

As described above, by one or more embodiments of the present invention, the elution peak of the antibody and/or antibody fragment becomes sharp and an amount of the acetate buffer as an eluate can be reduced. An amount of the acetate buffer to be used may be appropriately adjusted, and for example, the ratio to the volume of the affinity separation matrix may be 2 times or more by volume and 20 times or less by volume. When the ratio is 2 times or more by volume, the antibody and/or antibody fragment may eluted more surely. On the one hand, the ratio is 20 times or less by volume, an amount of the fraction containing the antibody and/or antibody fragment may be reduced and further purification may become easy. The above-described ratio may be more preferably 15 times or less by volume, more preferably not more than 10 times by volume or not more than 8 times by volume, and particularly preferably 5 times or less by volume. The volume of the affinity separation matrix as a standard means a volume of the affinity separation matrix measured by tapping the affinity separation matrix in a state of suspension and gel until the volume does not become reduced any more and leaving to stand.

Step 4: Posttreatment Step

By the above-described Step 3, an acetate buffer solution of the antibody and/or antibody fragment is obtained. The antibody and/or antibody fragment may be further purified by salting-out, chromatography, recrystallization or the like, and dried by freeze dry, spray dry, film drying method or the like.

Step 5: Step for Regenerating Affinity Separation Matrix

In the present step, the affinity separation matrix which is used in the above-described Step 3 and from which the antibody and/or antibody fragment is separated is regenerated by washing with an alkaline aqueous solution. It is not needed to necessarily perform the present step after the above-described Step 3, and the present step may be performed once every three iterations of the above Steps 1 to 3, once every five iterations, or once every ten iterations. Specifically, when a performance of the affinity separation matrix, such as binding capacity, is maintained, the present step is not necessarily performed. The implementation frequency and condition of the present step is different depending on the liquid sample containing the antibody and/or antibody fragment to be purified.

The "alkaline aqueous solution" usable for the regeneration of the affinity separation matrix means an aqueous solution which exhibits alkalinity to the extent that a purpose such as washing and sterilization can be achieved. More specifically, a sodium hydroxide aqueous solution of not less than 0.01 M and not more than 1.0 M or not less than 0.01 N and not more than 1.0 N is exemplified, but the alkaline aqueous solution is not restricted thereto. In the case of sodium hydroxide, the lower limit of the concentration may be preferably 0.01 M, more preferably 0.02 M, and even more preferably 0.05 M. On the one hand, the upper limit of sodium hydroxide concentration may be preferably 1.0 M, more preferably 0.5 M, even more preferably 0.3 M, even more preferably 0.2 M, and even more preferably 0.1 M. The alkaline aqueous solution is not necessarily a sodium hydroxide aqueous solution, and the pH thereof may be preferably 12 or more and 14 or less. With respect to the lower limit of the pH, 12.0 or more may be preferred, and 12.5 or more may be more preferred. With respect to the upper limit of the pH, 14 or less may be preferred, 13.5 or less may be more preferred, and 13.0 or less may be even more preferred.

The time to treat the affinity separation matrix after the above-described Step 3 by the alkaline aqueous solution is not particularly restricted and may be appropriately adjusted, since a damage degree of the peptide is different depending on the concentration of the alkaline aqueous solution and the temperature at the treatment. For example, when the concentration of sodium hydroxide is 0.05 M and the temperature during immersion is atmospheric temperature, the lower limit of the time to immerse the affinity separation matrix into the alkaline aqueous solution may be preferably 1 hour, more preferably 2 hours, more preferably 4 hours, more preferably 10 hour, and more preferably 20 hours, but is not particularly restricted as long as the affinity separation matrix can be regenerated.

The affinity separation matrix regenerated by the present step can be used in the above-described Steps 1 to 3 again.

The present application claims the benefit of the priority date of Japanese patent application No. 2016-94178 filed on May 9, 2016. All of the contents of the Japanese patent application No. 2016-94178 filed on May 9, 2016, are incorporated by reference herein.

EXAMPLES

Hereinafter, one or more embodiments of the present invention are described in more detail with Examples; however, the present invention is not restricted to the following Examples.

Example 1

(1) Preparation of Commercially Available Affinity Separation Matrix As the affinity separation matrix which could adsorb an antibody fragment containing κ-chain variable region (VL-κ), "HiTrap Protein L 1 mL-gel" manufactured by GE Healthcare was obtained and installed in a chromatography system. The term "1 mL-gel" means that the volume of the affinity separation matrix measured by tapping or standing still a suspension of the affinity separation matrix until the volume of the affinity separation matrix in a state of gel does not become reduced any more is 1 mL.

(2) Experimental Production of Affinity Separation Matrix

In order to confirm the effect of an acetate buffer on an affinity separation matrix except for the above-described commercially available affinity separation matrix, an affinity separation matrix which could adsorb an antibody fragment containing VL-κ was experimentally produced. Specifically, a VL-κ-binding peptide was designed. In the VL-κ-binding peptide, 4 VL-κ-binding domains (SEQ ID NO: 2) which were contained in wild Protein L (SEQ ID NO: 1) derived from *Peptostreptococcus magnus* 312 strain were bound through peptides which connected domains in SEQ ID NO: 1, and an active group for immobilizing the peptide on a carrier was added at the C-terminal. The base sequence which encoded the peptide was designed by conducting reverse translation on the basis of the designed amino acid sequence. The DNA which had the base sequence, PstI recognition site at 5' end and XbaI recognition site at 3' end was synthesized as an artificial synthetic gene by outsourcing to Eurofins Genomics K. K. The expression plasmid for subcloning was digested by restriction enzyme PstI and XbaI manufactured by Takara Bio Inc. to obtain a DNA fragment. An expression vector pNCMO2 for *Brevibacillus* Expression System manufactured by Takara Bio Inc. was digested by the same restriction enzyme, and the obtained DNA fragment was ligated thereto to obtain an expression vector prepared by inserting DNA which encoded the amino acid sequence of the above-described VL-κ-binding peptide into an expression vector pNCMO2 for *Brevibacillus* Expression System. The ligation reaction was performed by using a ligation reagent ("Ligation high" manufactured by TOYOBO CO., LTD.) in accordance with the protocol attached to the product, and *Escherichia coli* JM109 strain manufactured by Takara Bio Inc. was used for preparing the plasmid. The base sequence of each expression plasmid DNA was confirmed by using DNA sequencer 3130×1 Genetic Analyzer manufactured by Applied Biosystems. A sequencing PCR reaction of each plasmid DNA was performed by using BigDye Terminator v.1.1 Cycle Sequencing Kit manufactured by Applied Biosystems in accordance with the protocol attached to the product, and the obtained sequencing product was purified by using a plasmid purification kit ("BigDye XTerminator Purification Kit" manufactured by Applied Biosystems) in accordance with the protocol attached to the product to be used for sequence analysis.

*Brevibacillus choshinensis* SP3 strain manufactured by Takara Bio Inc. was transformed by the obtained plasmid, and the genetically modified bacterium which produced and secreted the above-described VL-κ-binding peptide was cultivated. The genetically modified bacterium was cultivated in 30 mL of A culture medium (polypeptone 3.0%, yeast extract 0.5%, glucose 3%, magnesium sulfate 0.01%, ferric sulfate 0.001%, manganese chloride 0.001%, zinc chloride 0.0001%) containing 60 μg/mL of neomycin with shaking at 30° C. for 3 days. After the cultivation, the culture medium was subjected to centrifugation at 15,000 rpm and 25° C. for 5 minutes to remove the bacterial body.

The above-described VL-κ-binding peptide was purified from the obtained culture supernatant by cation exchange chromatography for which a cation exchange carrier ("UnoSphere S" manufactured by Bio-Rad) was used. A column ("Tricorn 10/200" manufactured by GE Healthcare Bioscience) was filled with the UnoSphere S. Specifically, sodium acetate was added to the culture supernatant at a final concentration of 50 mM, and the pH thereof was adjusted to 4.0 by acetic acid. The UnoSphere S column was equilibrated by buffer A for cation exchange (50 mM $CH_3COOH$—$CH_3COONa$, pH 4.0), and the culture supernatant was added into the column. After the column was washed by the buffer A for cation exchange, VL-κ-binding peptide was eluted to be obtained by using salt concentration gradient with the buffer A for cation exchange and buffer B for cation exchange (50 mM $CH_3COOH$—$CH_3COONa$, 1 M NaCl, pH 4.0) Then, the VL-κ-binding peptide was purified by anion exchange chromatography for which an anion exchange carrier ("Nuvia Q" manufactured by Bio-Rad) was used. A column ("Tricorn 10/200" manufactured by GE Healthcare Bioscience) was filled with the Nuvia Q. Specifically, the obtained VL-κ-binding peptide solution was dialyzed by using a buffer A for anion exchange (50 mM Tris-HCl, pH 8.0). The Nuvia Q column was equilibrated by buffer A for anion exchange, and the solution was added into the column. After the column was washed by the buffer A for anion exchange, VL-κ-binding peptide was eluted to be obtained by using salt concentration gradient with the buffer A for anion exchange and buffer B for anion exchange (50 mM Tris-HCl, 1.0 M NaCl, pH 8.0). The obtained VL-κ-binding peptide was dialyzed by using ultrapure water, and an aqueous solution containing the VL-κ-binding peptide only was obtained as a final purified sample. The above-described protein purification by chromatography with a column was performed by using a chromatography system ("AKTAavant 25 system" manufactured by GE Healthcare Bioscience). The obtained VL-κ-binding peptide was immobilized on a commercially available agarose carrier.

Specifically, first, 1.5 mL-gel of commercially available NHS-activated carrier ("NHS Activated Sepharose 4 Fast Flow" manufactured by GE Healthcare Bioscience) was transferred on a glass filter, and isopropanol as a preservation liquid was removed by suction, and then the carrier was washed by iced 1 mM hydrochloric acid (5 mL). Next, after the carrier was washed by 5 mL of a coupling buffer (20 mM $NaH_2PO_4$—$Na_2HPO_4$, 150 mM sodium chloride, pH 7.2), the washed carrier was collected with suspending in the coupling buffer and transferred into a centrifuge tube. N-[ε-Maleimidocaproic acid]hydrazide.TFA (EMCH, manufactured by Thermo Fisher Scientific Inc.) was dissolved in the coupling buffer to obtain 10 mM solution, and the solution was added into the centrifuge tube with the carrier for the reaction at 25° C. for 1 hour. Then, the carrier was transferred on a glass filter, and washed with 10 mL of washing buffer A (0.5 M ethanolamine, 0.5 M sodium chloride, pH 7.2), 10 mL of the coupling buffer and 10 mL of the washing buffer A in this order, and left to stand at 25° C. for 15 minutes. The carrier was further washed with the coupling buffer (10 mL). According to the preceding procedure, maleimide was bound to the carrier.

Next, the carrier bound by maleimide was transferred into a centrifuge tube, and the VL-κ-binding peptide solution was added thereto for the reaction at 25° C. for 2 hours. Then, the reacted carrier was transferred on a glass filter, and washed with 7 mL of the coupling buffer to recover the unreacted VL-K-binding peptide. Thereafter, the carrier was washed with 10 mL of a washing buffer B (50 mM L-cysteine, 100 mM $NaH_2PO_4$—$Na_2HPO_4$, 0.5 M sodium chloride, pH 7.2), 10 mL of the coupling buffer and 10 mL of the washing buffer B in this order, and then the carrier was left to stand at 25° C. for 15 minutes. After the carrier was further washed with 10 mL of the coupling buffer, 10 mL of ultrapure water and 10 mL of 20% ethanol, the carrier was suspended in 20% ethanol and collected to obtain affinity separation matrix having the above-described VL-κ-binding peptide as a ligand (Experimental product A).

An absorbance of the collected unreacted VL-κ-binding peptide at 280 nm was measured by using a spectrometer, and an amount of the unreacted VL-κ-binding peptide was calculated on the basis of the absorption coefficient calculated from the amino acid sequence. The amount of the immobilized VL-κ-binding peptide was calculated on the basis of the difference between the amount of the originally-used VL-κ-binding peptide and the determined amount of the unreacted VL-κ-binding peptide, and the ligand density was further calculated on the basis of the volume of the carrier. As a result, the ligand density of the Experimental product A was 10 mg/mL-gel.

In addition, a VL-κ-binding peptide was designed and prepared similarly to the above, in which peptide 4 VL-κ-binding domain variants having the amino acid sequence of SEQ ID NO: 3 were bound through peptides which connected domains in SEQ ID NO: 1, and was immobilized on a carrier to prepare an affinity separation matrix (Experimental product B). The ligand density of the Experimental product B was 12.5 mg/mL-gel.

A commercially available column ("Tricorn 5/50" manufactured by GE Healthcare) was filled with 1 mL-gel of each affinity separation matrix of Experimental product A or Experimental product B.

(3) Preparation of Fab Fragment Derived from IgG

As a VL-κ-containing peptide, a Fab fragment (IgG-Fab) was selected. A humanized monoclonal antibody IgG drug product containing VL-κ was used as a raw material, and the product was fragmented into Fab fragment and Fc fragment by using papain. The Fab fragment only was separated and purified. Hereinafter, a method for preparing Fab derived from anti-IgE monoclonal antibody (generic name: "Omalizumab") is described, but other monoclonal Fab can be basically prepared by a similar method.

Specifically, in the case of a humanized monoclonal antibody IgG drug product, "Xolair" manufactured by Novartis AG was dissolved in a buffer for papain digestion (0.1 M AcOH—AcONa, 2 mM EDTA, 1 mM cysteine, pH 5.5). Agarose on which papain was immobilized ("Papain Agarose from *papaya* latex" manufactured by SIGMA) was added thereto. The mixture was incubated at 37° C. for about 8 hours while the mixture was stirred by a rotator. The reaction mixture containing both of Fab fragment and Fc fragment was separated from the agarose on which papain was immobilized. A Fab solution was obtained as a flow-through fraction by affinity chromatography using KANEKA KanCapA™ column manufactured by KANEKA CORPORATION from the reaction mixture. The obtained Fab solution was subjected to purification by gel filtration chromatography using Superdex 75 10/300 GL column to obtain a Fab solution. A standard buffer was used for equilibrating and separation. The above protein purification by chromatography was performed by using AKTAavant 25 system.

(4) Elution Test

After Fab was adsorbed on the affinity separation matrix on which an antibody fragment containing VL-κ could be adsorbed, pH at the elution peak top of Fab was identified by using pH gradient. As the affinity separation matrix on which an antibody fragment containing VL-κ could be adsorbed, a commercially available product used in the above (1) ("HiTrap Protein L" manufactured by GE Healthcare) and Experimental product A and Experimental product B which were prepared in the above (2) were used. The following procedure was performed at 25° C.

Specifically, AKTAavant 25 system manufactured by GE Healthcare was used as a chromatography system, and a column which was filled with the commercially available product, Experimental product A or Experimental product B was connected thereto. The column was equilibrated by an equilibrating buffer (20 mM $NaH_2PO_4$—$Na_2HPO_4$, 150 mM NaCl, pH 7.4). To the column, 1 mg of the Fab prepared by the above (3) was added. After 3 CV (column volume) of the equilibrating buffer was flown through the column, Fab was eluted by 100 mM acetate buffer with linear pH gradient from pH 5.0 to pH 3.0. More specifically, after the column was equilibrated by 5 CV of acetate buffer A (100 mM acetate buffer, pH 5.0), when 20 CV of a buffer was flown through the column, the concentration of acetate buffer B (100 mM acetate buffer, pH 3.0) was increased from 0% to 100% in a linear manner and the elution pH was identified on the basis of the position of Fab elution. With respect to Fab elution pH in the case where a citrate buffer as a reference was used, similarly to the above, after the column was equilibrated by 5 CV of citrate buffer A (100 mM citrate buffer, pH 5.0), when 20 CV of a buffer was flown through the column, the concentration of citrate buffer B (100 mM citrate buffer, pH 2.4) was increased from 0% to 100% in a linear manner and the elution pH was identified on the basis of the position of Fab elution. In the above procedure, all of the flow rate were adjusted to 0.3 mL/min. The result of Fab elution pH was collectively shown in Table 1.

TABLE 1

| Affinity separation matrix | Antibody elution pH | | |
|---|---|---|---|
| | 100 mM citrate buffer | 100 mM acetate buffer | Δ pH (acetate buffer value − citrate buffer value) |
| Commercial product | 2.93 | 3.60 | 0.67 |
| A | 2.71 | 3.47 | 0.76 |
| B | 2.85 | 3.53 | 0.68 |

As the result shown in Table 1, it was proved that when a acetate buffer is used, the pH of Fab elution substantially becomes higher by 0.6 or more in comparison with the case where a citrate buffer is used in all of the cases of a commercially available product, Experimental product A and Experimental product B. Since a similar tendency is observed in any cases of a commercially available product, Experimental product A and Experimental product B, the improvement effect of an acetate buffer on elution pH of Fab is considered to be effective on the affinity separation matrixes having Protein L and variant Protein L as a ligand.

Example 2

(1) Elution Test Using Eluate of pH 3.0

After Fab was adsorbed on the affinity separation matrix on which an antibody fragment containing VL-κ could be adsorbed, an elution test of Fab was performed. As the affinity separation matrix on which an antibody fragment containing VL-κ could be adsorbed, a commercially available product ("HiTrap Protein L" manufactured by GE Healthcare), Experimental product A and Experimental product B were used. A column was filled with the product, and connected to AKTAavant 25. The following experiment was performed at 25° C.

The column was equilibrated by an equilibrating buffer (20 mM $NaH_2PO_4$—$Na_2HPO_4$, 150 mM NaCl, pH 7.4). To the column, 3 mg of the Fab prepared by the above Example 1(3) was added. After 10 CV (column volume) of the equilibrating buffer was flown through the column, 10 CV of 100 mM acetate buffer (pH 3.0) was flown through the column as an eluate. After 3 CV of the equilibrating buffer was flown, 10 CV of a strong washing liquid (100 mM citrate buffer, pH 2.4) was flown to elute the Fab remaining in the column. Finally, 5 CV of the equilibrating buffer was flown to finish the test. As a reference, the test using 100 mM citrate buffer (pH 3.0) as an eluate was also performed.

As FIG. 1, chromatograms in the case where an acetate buffer and a citrate buffer were used as an eluate in a commercially available affinity separation matrix are shown. When a citrate buffer was used, 7.6 CV of an eluate was needed to approximately completely elute Fab; on the one hand, when an acetate buffer was used, 1.2 CV of an eluate was needed to approximately completely elute Fab.

Figure 2:
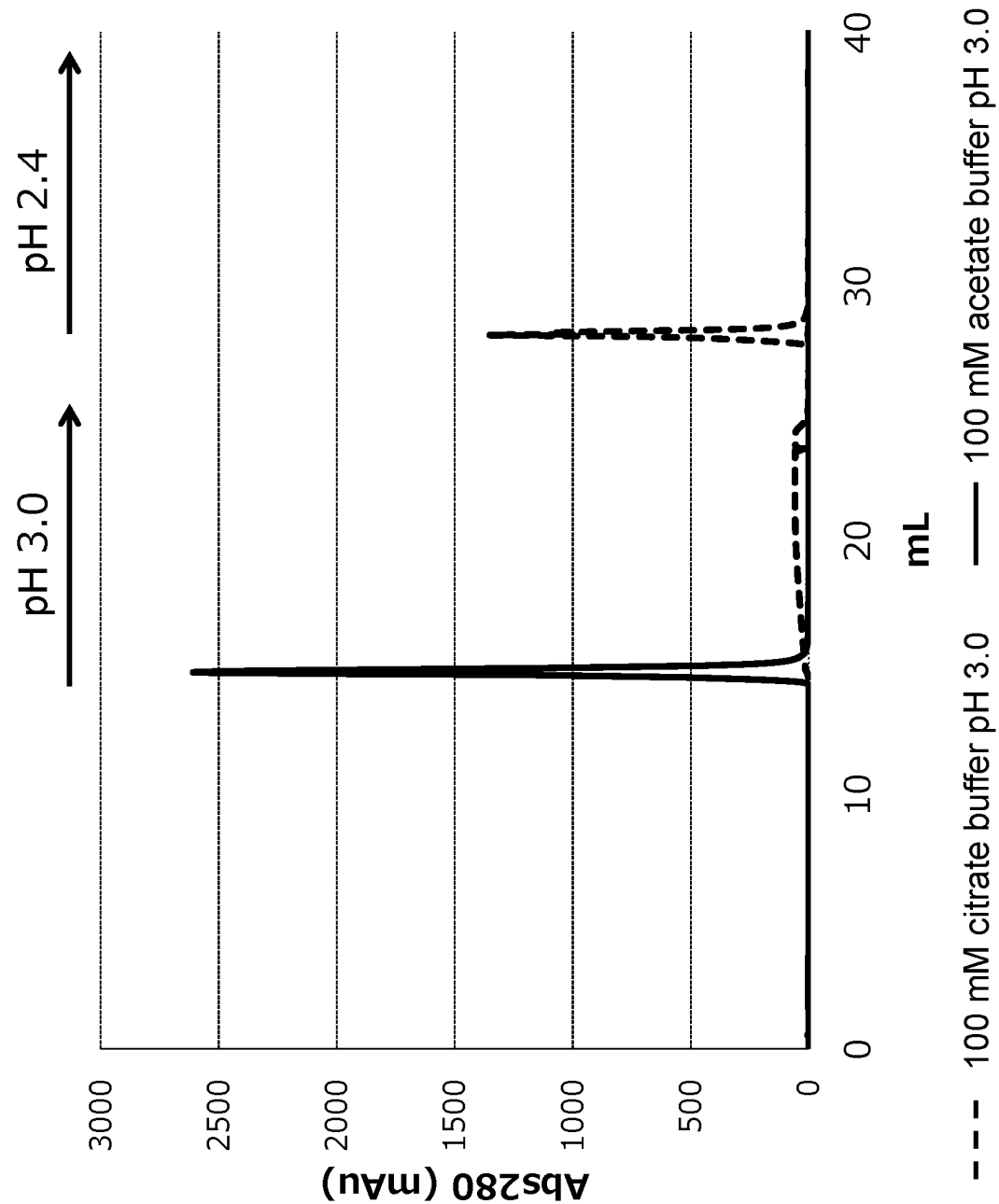
FIG. 2 represents an elution profile in the case where an acetate buffer or a citrate buffer having pH of 3.0 was used as an eluate, when a Fab fragment containing VL-κ was purified by using an experimentally-produced affinity separation matrix on which Protein L was immobilized. A citrate buffer having pH of 2.4 was also used in order to dissociate a Fab fragment remaining in the matrix.

FIG. 2 demonstrates the result of the affinity separation matrix of Experimental product A. When a citrate buffer was used, Fab was not completely eluted even by 10 CV of an eluate and Fab was eluted in a strong washing fraction; on the one hand, when an acetate buffer was used, Fab was approximately completely eluted by flowing 1.5 CV of an eluate.

Figure 3:
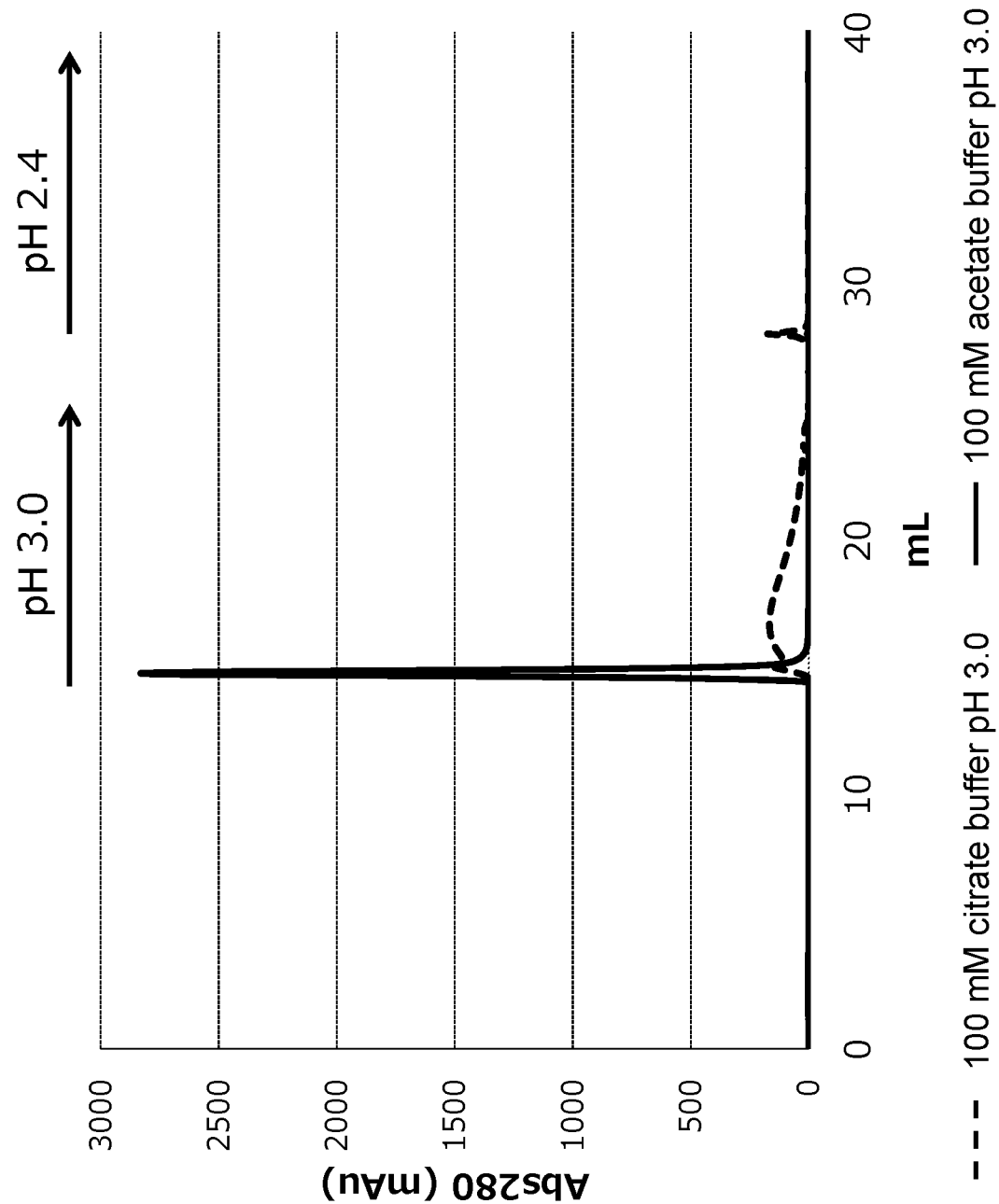
FIG. 3 represents an elution profile in the case where an acetate buffer or a citrate buffer having pH of 3.0 was used as an eluate, when a Fab fragment containing VL-κ was purified by using an experimentally-produced affinity separation matrix on which variant Protein L was immobilized. A citrate buffer having pH of 2.4 was also used in order to dissociate a Fab fragment remaining in the matrix.

FIG. 3 demonstrates the result of the affinity separation matrix of Experimental product B. When a citrate buffer was used, Fab was not completely eluted even by 10 CV of an eluate and Fab was eluted in a strong washing fraction; on the one hand, when an acetate buffer was used, Fab was approximately completely eluted by flowing 1.2 CV of an eluate.

From the above results, it was found that when an acetate buffer is used, an elution peak becomes sharper in all of matrixes. In addition, when an acetate buffer is used, a volume of an elution fraction of a VL-κ-containing peptide can be substantially reduced in comparison with a citrate buffer and a VL-κ-containing peptide can be purified more easily.

(2) Elution Test Using Eluate of pH 3.5

Figure 4:
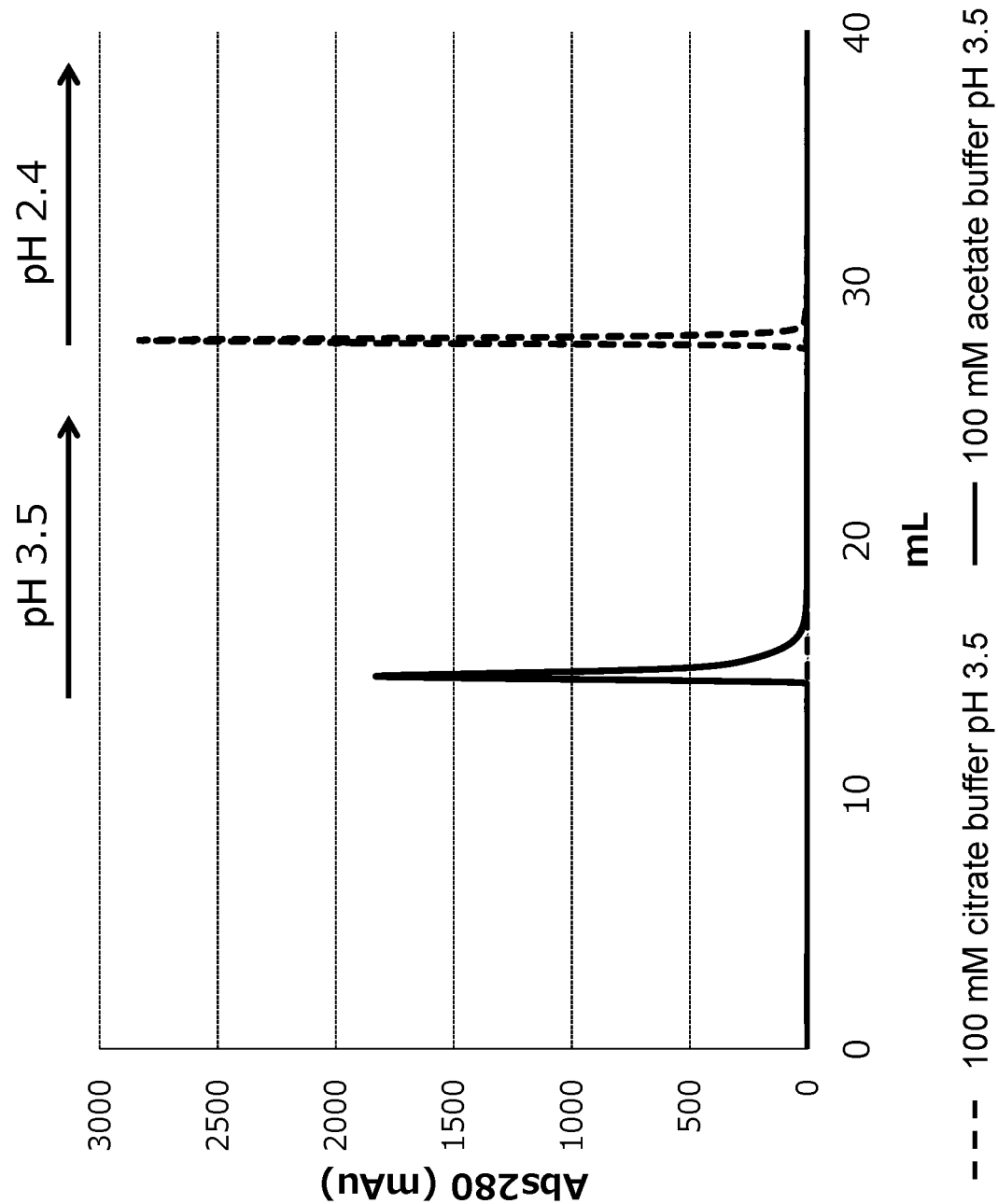
FIG. 4 represents an elution profile in the case where an acetate buffer or a citrate buffer having pH of 3.5 was used as an eluate, when a Fab fragment containing VL-κ was purified by using a commercially available affinity separation matrix on which Protein L was immobilized. A citrate buffer having pH of 2.4 was also used in order to dissociate a Fab fragment remaining in the matrix.

With respect to the commercially available product, the evaluation in the case where an eluate of pH 3.5 was used was performed similarly to the above (1). The result is shown in FIG. 4. It was found from the comparison of the chromatograms of FIG. 4 that when a citrate buffer was used, Fab was not eluted at all even by flowing the eluate and Fab remaining in the column was eluted in a strong washing fraction. On the one hand, when an acetate buffer was used, Fab was completely eluted by flowing 2.9 CV of the eluate. It was found from the results that Fab can be eluted by using an acetate buffer even at the pH at which it is difficult to elute Fab by a citrate buffer.

Comparative Example 1

As a comparative example, an antibody elution test in the case where an acetate buffer and a citrate buffer were used as an eluate for other affinity separation matrix was performed. As the affinity separation matrix, a commercially available Protein A carrier ("HiTrap MabSelect SuRe" manufactured by GE Healthcare) (1 mL), which is generally used for purifying an antibody, was used. Since Protein A carrier hardly adsorbs Fab, IgG was used as a test antibody. As IgG, a humanized monoclonal antibody product (anti-IgE monoclonal antibody, "Xolair" manufactured by Novartis AG) described above was used.

First, an antibody elution test was performed similarly to the above-described Example 1(4) except that the above-described commercially available Protein A carrier was used in place of Protein L carrier. Specifically, AKTAavant 25 system manufactured by GE Healthcare was used as a chromatography system, a column was filled with the commercially available Protein A carrier, and the column was connected to the system. The column was equilibrated by an equilibrating buffer (20 mM $NaH_2PO_4$—$Na_2HPO_4$, 150 mM NaCl, pH 7.4). To the equilibrated column, 1 mg of the humanized monoclonal IgG was added. After 3 CV (column volume) of the equilibrating buffer was flown through the column, IgG was eluted by 100 mM acetate buffer with linear pH gradient from pH 5.0 to pH 3.0. More specifically, after the column was equilibrated by 5 CV of acetate buffer A (100 mM acetate buffer, pH 5.0), when 20 CV of a buffer was flown through the column, the concentration of acetate buffer B (100 mM acetate buffer, pH 3.0) was increased from 0% to 100% in a linear manner and the elution pH was identified on the basis of the position of IgG elution. With respect to IgG elution pH in the case where a citrate buffer was used as a reference, similarly to the above, after the column was equilibrated by 5 CV of citrate buffer A (100 mM citrate buffer, pH 5.0), when 20 CV of a buffer was flown through the column, the concentration of citrate buffer B (100 mM citrate buffer, pH 2.4) was increased from 0% to 100% in a linear manner and the elution pH was identified on the basis of the position of IgG elution. In the above procedure, all of the flow rate were adjusted to 0.3 mL/min. The obtained result of the elution pH of the humanized monoclonal IgG was collectively shown in Table 2.

TABLE 2

| | Antibody elution pH | | |
|---|---|---|---|
| Affinity separation matrix | 100 mM citrate buffer | 100 mM acetate buffer | Δ pH (acetate buffer value − citrate buffer value) |
| Commercial Protein A carrier | 3.53 | 3.64 | 0.11 |

As the result shown in Table 2, when the affinity separation matrix having Protein A as a ligand was used, ΔpH was substantially smaller as 0.11 in comparison with the case where the affinity separation matrix had Protein L as a ligand, in which ΔpH was 0.67 to 0.76 as shown in Table 1. In other words, it was found that the improvement effect by an acetate buffer on elution pH of an antibody is much effective on the affinity separation matrix having Protein L as a ligand.

Comparative Example 2

After IgG was adsorbed on the above-described commercially available Protein A carrier, IgG was eluted for experiment. A column was filled with the commercially available Protein A carrier, and the column was connected to AKTAavant 25. The following experiment was performed at 25° C. Similarly to the above Example 2(1), the column was equilibrated by an equilibrating buffer (20 mM $NaH_2PO_4$—$Na_2HPO_4$, 150 mM NaCl, pH 7.4). To the column, 3 mg of the humanized monoclonal IgG was added. After 10 CV (column volume) of the equilibrating buffer was flown through the column, 10 CV of 100 mM acetate buffer (pH 3.0) was flown through the column as an eluate. After 3 CV of the equilibrating buffer was further flown, 10 CV of a strong washing liquid (100 mM citrate buffer, pH 2.4) was flown to eluate the IgG remaining in the column. Finally, 5 CV of the equilibrating buffer was flown to finish the test. As a reference, the test using 100 mM citrate buffer (pH 3.0) as an eluate was also performed.

Figure 5:
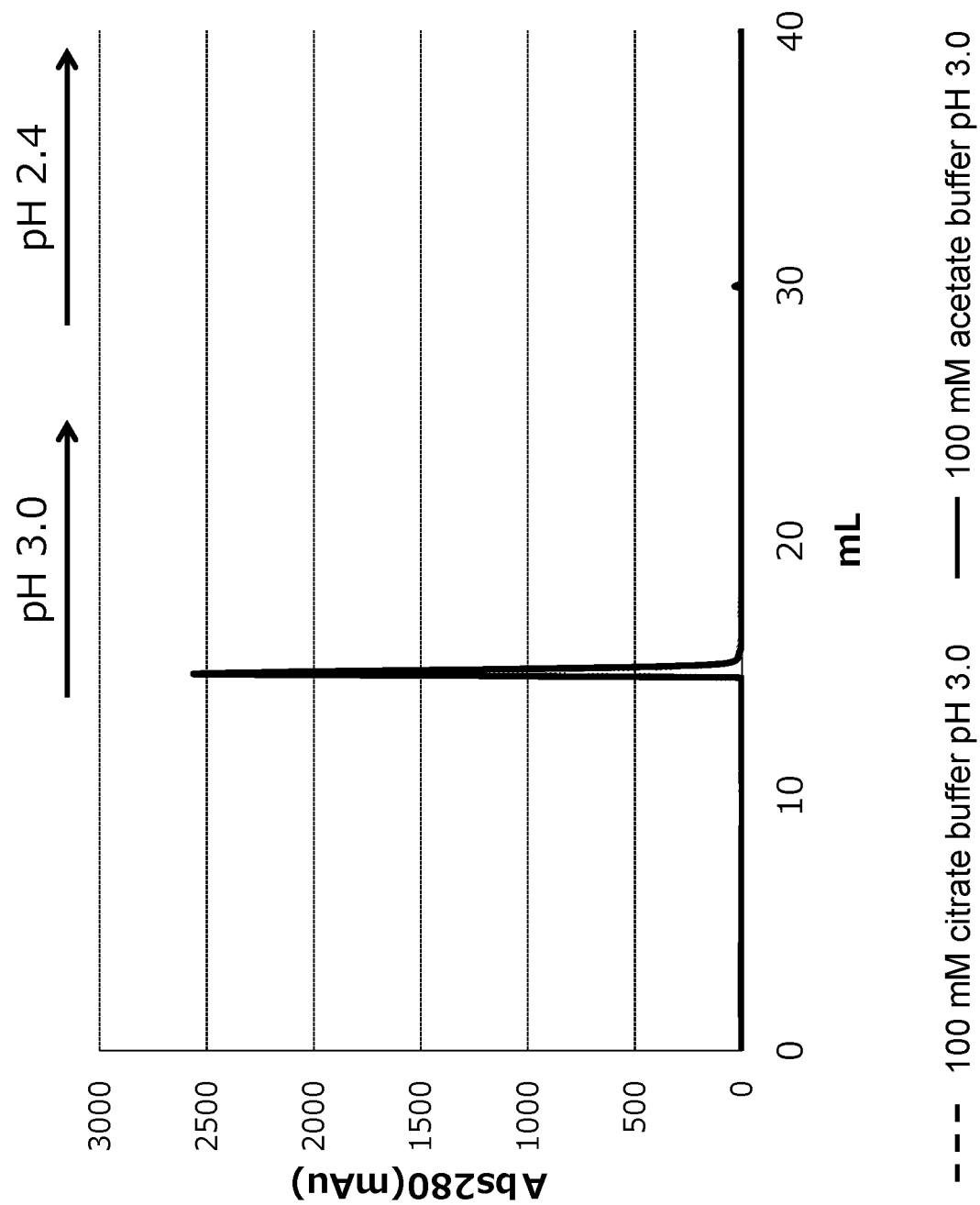
FIG. 5 represents a figure to compare elution profiles in the case where an acetate buffer or a citrate buffer having pH of 3.0 was used as an eluate, when IgG was purified by using a commercially available affinity separation matrix on which Protein A was immobilized. A citrate buffer having pH of 2.4 was also used in order to dissociate IgG remaining in the matrix.

As FIG. 5, chromatograms in the case where an acetate buffer and a citrate buffer were used as an eluate for a commercially available Protein A carrier are shown. As the result shown in FIG. 5, when a citrate buffer was used and when an acetate buffer was used, the elution curves were nearly completely overlapped. In both of cases, IgG was nearly completely eluted by 1.2 CV of an eluate, and there was no difference in the amount of eluate due to the difference between an acetate buffer and a citrate buffer.

Comparative Example 3

After IgG was adsorbed on the commercially available Protein A carrier, IgG was eluted for experiment. The pH of the eluate was changed from that of the above-described Comparative Example 2. A column was filled with the commercially available Protein A carrier, and the column was connected to AKTAavant 25. The following experiment was performed at 25° C. Similarly to the above-described Comparative example 2, the column was equilibrated by an equilibrating buffer (20 mM $NaH_2PO_4$—$Na_2HPO_4$, 150 mM NaCl, pH 7.4). To the column, 3 mg of the humanized monoclonal IgG was added. After 10 CV (column volume) of the equilibrating buffer was flown through the column, 10 CV of 100 mM acetate buffer (pH 3.5) was flown through the column as an eluate. After 3 CV of the equilibrating buffer was further flown, 10 CV of a strong washing liquid (100 mM citrate buffer, pH 2.4) was flown to eluate the IgG remaining in the column. Finally, 5 CV of the equilibrating buffer was flown to finish the test. As a reference, the test using 100 mM citrate buffer (pH 3.5) as an eluate was also performed.

Figure 6:
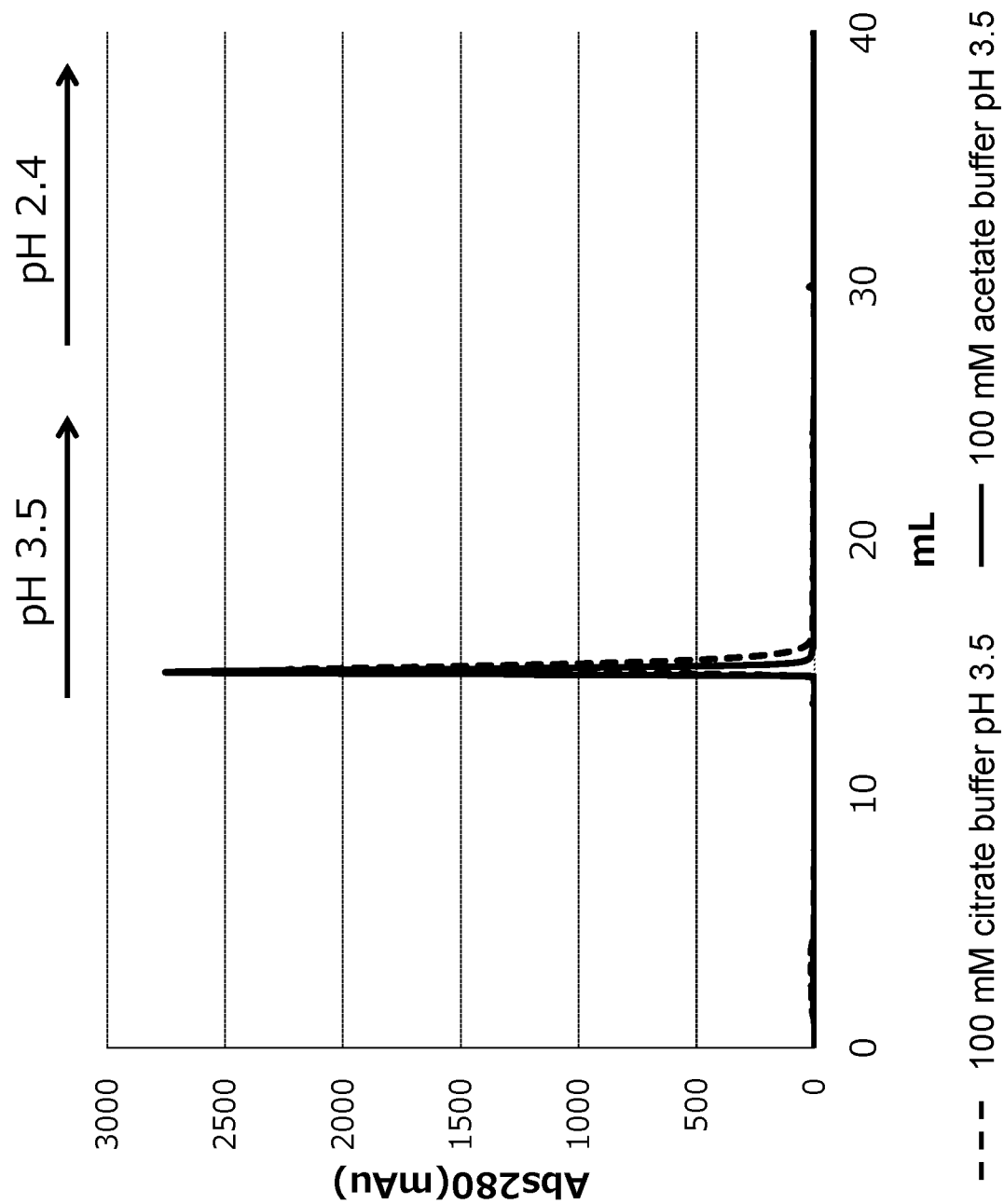
FIG. 6 represents a figure to compare elution profiles in the case where an acetate buffer or a citrate buffer having pH of 3.5 was used as an eluate, when IgG was purified by using a commercially available affinity separation matrix on which Protein A was immobilized. A citrate buffer having pH of 2.4 was also used in order to dissociate IgG remaining in the matrix.

As FIG. 6, chromatograms in the case where an acetate buffer and a citrate buffer were used as an eluate for a commercially available Protein A carrier are shown. When an acetate buffer was used, IgG was nearly completely eluted by 1.3 CV of an eluate. When a citrate buffer was used, IgG was nearly completely eluted by 1.9 CV of an eluate. Under the relatively high acidic pH condition, amounts of an eluate were different from each other between the cases of an acetate buffer and a citrate buffer but the difference was small.

From the results of Comparative example 2 and Comparative example 3, it was confirmed that the effect on the reduction of elution fraction amount (antibody elution solution amount) in the case where an acetate buffer is used for a commercially available Protein A carrier is smaller than that the case for a Protein L carrier. Specifically, in Example 2 using a Protein L carrier, when an acetate buffer was used as an eluate, an amount of elution fraction was reduced by 6.4 CV and by 84% in comparison with the case where a citrate buffer was used as an eluate. On the one hand, in Comparative example 2 using a commercially available Protein A, amounts of an eluate were almost the same between the cases of a citrate buffer and an acetate buffer. In addition, in Comparative example 3 using a commercially available Protein A, when an acetate buffer was used as an eluate, an amount of elution fraction was reduced by 0.6 CV only and a reduction rate was mere 32% in comparison with the case where a citrate buffer was used as an eluate. Thus, it was found that an acetate buffer has a profound effect on an elution of an antibody which is adsorbed on a Protein L carrier.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A method for purifying an antibody or an antibody fragment containing κ-chain variable region, comprising:
    adsorbing at least one of the antibody or the antibody fragment onto an affinity separation matrix at a temperature ranging from 4 to 40° C. by contacting a liquid sample with the affinity separation matrix;
    washing the affinity separation matrix to remove impurities; and
    separating the at least one of the antibody or the antibody fragment from the affinity separation matrix at a temperature ranging from 4 to 40° C. by using an acetate buffer,
    wherein the acetate buffer has a pH value of 2.5 to 4.0 and an acetate ion concentration of 10 to 500 mM,
    wherein the liquid sample comprises the at least one of the antibody or the antibody fragment,
    wherein the affinity separation matrix comprises: a water-insoluble carrier; and a ligand selected from the group consisting of Protein L, a variant of Protein L, a domain of Protein L, and a variant of the domain, and
    wherein the ligand is immobilized on the water-insoluble carrier.

2. The method according to claim 1, wherein the pH value of the acetate buffer is 2.8 to 3.8.

3. The method according to claim 1, wherein the acetate ion concentration is 50 to 400 mM.

* * * * *

SEQUENCE LISTING

<160> NUMBER OF SEQ ID NOS: 3

<210> SEQ ID NO 1
<211> LENGTH: 719
<212> TYPE: PRT
<213> ORGANISM: Peptostreptococcus magnus

<400> SEQUENCE: 1

```
Met Ala Ala Leu Ala Gly Ala Ile Val Val Thr Gly Gly Val Gly Ser
1               5                   10                  15

Tyr Ala Ala Asp Glu Pro Ile Asp Leu Glu Lys Leu Glu Glu Lys Arg
            20                  25                  30

Asp Lys Glu Asn Val Gly Asn Leu Pro Lys Phe Asp Asn Glu Val Lys
        35                  40                  45

Asp Gly Ser Glu Asn Pro Met Ala Lys Tyr Pro Asp Phe Asp Glu
    50                  55                  60

Ala Ser Thr Arg Phe Glu Thr Glu Asn Asn Glu Phe Glu Glu Lys Lys
65                  70                  75                  80

Val Val Ser Asp Asn Phe Phe Asp Gln Ser Glu His Pro Phe Val Glu
                85                  90                  95

Asn Lys Glu Glu Thr Pro Glu Thr Pro Glu Thr Asp Ser Glu Glu Glu
            100                 105                 110

Val Thr Ile Lys Ala Asn Leu Ile Phe Ala Asn Gly Ser Thr Gln Thr
        115                 120                 125

Ala Glu Phe Lys Gly Thr Phe Glu Lys Ala Thr Ser Glu Ala Tyr Ala
    130                 135                 140

Tyr Ala Asp Thr Leu Lys Lys Asp Asn Gly Glu Tyr Thr Val Asp Val
145                 150                 155                 160

Ala Asp Lys Gly Tyr Thr Leu Asn Ile Lys Phe Ala Gly Lys Glu Lys
                165                 170                 175

Thr Pro Glu Glu Pro Lys Glu Glu Val Thr Ile Lys Ala Asn Leu Ile
            180                 185                 190

Tyr Ala Asp Gly Lys Thr Gln Thr Ala Glu Phe Lys Gly Thr Phe Glu
        195                 200                 205

Glu Ala Thr Ala Glu Ala Tyr Arg Tyr Ala Asp Ala Leu Lys Lys Asp
    210                 215                 220

Asn Gly Glu Tyr Thr Val Asp Val Ala Asp Lys Gly Tyr Thr Leu Asn
225                 230                 235                 240

Ile Lys Phe Ala Gly Lys Glu Lys Thr Pro Glu Glu Pro Lys Glu Glu
                245                 250                 255

Val Thr Ile Lys Ala Asn Leu Ile Tyr Ala Asp Gly Lys Thr Gln Thr
            260                 265                 270

Ala Glu Phe Lys Gly Thr Phe Glu Ala Thr Ala Glu Ala Tyr Arg
        275                 280                 285

Tyr Ala Asp Leu Leu Ala Lys Glu Asn Gly Lys Tyr Thr Val Asp Val
    290                 295                 300
```

-continued

```
Ala Asp Lys Gly Tyr Thr Leu Asn Ile Lys Phe Ala Gly Lys Glu Lys
305                 310                 315                 320

Thr Pro Glu Glu Pro Lys Glu Val Thr Ile Lys Ala Asn Leu Ile
                325                 330                 335

Tyr Ala Asp Gly Lys Thr Gln Thr Ala Glu Phe Lys Gly Thr Phe Ala
                340                 345                 350

Glu Ala Thr Ala Glu Ala Tyr Arg Tyr Ala Asp Leu Leu Ala Lys Glu
                355                 360                 365

Asn Gly Lys Tyr Thr Ala Asp Leu Glu Asp Gly Gly Tyr Thr Ile Asn
                370                 375                 380

Ile Arg Phe Ala Gly Lys Lys Val Asp Glu Lys Pro Glu Glu Lys Glu
385                 390                 395                 400

Gln Val Thr Ile Lys Glu Asn Ile Tyr Phe Glu Asp Gly Thr Val Gln
                405                 410                 415

Thr Ala Thr Phe Lys Gly Thr Phe Ala Glu Ala Thr Ala Glu Ala Tyr
                420                 425                 430

Arg Tyr Ala Asp Leu Leu Ser Lys Glu His Gly Lys Tyr Thr Ala Asp
                435                 440                 445

Leu Glu Asp Gly Gly Tyr Thr Ile Asn Ile Arg Phe Ala Gly Lys Glu
450                 455                 460

Glu Pro Glu Glu Thr Pro Glu Lys Pro Glu Val Gln Asp Gly Tyr Ala
465                 470                 475                 480

Ser Tyr Glu Glu Ala Glu Ala Ala Lys Glu Ala Leu Lys Asn Asp
                485                 490                 495

Asp Val Asn Lys Ser Tyr Thr Ile Arg Gln Gly Ala Asp Gly Arg Tyr
                500                 505                 510

Tyr Tyr Val Leu Ser Pro Val Glu Ala Glu Glu Lys Pro Glu Ala
                515                 520                 525

Gln Asn Gly Tyr Ala Thr Tyr Glu Glu Ala Glu Ala Ala Lys Lys
                530                 535                 540

Ala Leu Glu Asn Asp Pro Ile Asn Lys Ser Tyr Ser Ile Arg Gln Gly
545                 550                 555                 560

Ala Asp Gly Arg Tyr Tyr Tyr Val Leu Ser Pro Val Glu Ala Glu Thr
                565                 570                 575

Pro Glu Lys Pro Val Glu Pro Ser Glu Pro Thr Pro Asp Val Pro
                580                 585                 590

Ser Asn Pro Ser Asn Pro Ser Thr Pro Asp Val Pro Ser Thr Pro Asp
                595                 600                 605

Val Pro Ser Asn Pro Ser Thr Pro Glu Val Pro Ser Asn Pro Ser Thr
                610                 615                 620

Pro Gly Asn Glu Glu Lys Pro Gly Asn Glu Gln Lys Pro Gly Asn Glu
625                 630                 635                 640

Gln Lys Pro Gly Asn Glu Gln Lys Pro Gly Asn Glu Gln Lys Pro Gly
                645                 650                 655

Asn Glu Gln Lys Pro Asp Gln Pro Ser Lys Pro Glu Lys Glu Glu Asn
                660                 665                 670

Gly Lys Gly Gly Val Asp Ser Pro Lys Lys Glu Lys Ala Ala Leu
                675                 680                 685

Pro Lys Ala Gly Ser Glu Ala Glu Ile Leu Thr Leu Ala Ala Ala Ser
690                 695                 700

Leu Ser Ser Val Ala Gly Ala Phe Ile Ser Leu Lys Lys Arg Lys
705                 710                 715
```

```
<210> SEQ ID NO 2
<211> LENGTH: 63
<212> TYPE: PRT
<213> ORGANISM: Peptostreptococcus magnus

<400> SEQUENCE: 2

Glu Gln Val Thr Ile Lys Glu Asn Ile Tyr Phe Glu Asp Gly Thr Val
1               5                   10                  15

Gln Thr Ala Thr Phe Lys Gly Thr Phe Ala Glu Ala Thr Ala Glu Ala
            20                  25                  30

Tyr Arg Tyr Ala Asp Leu Leu Ser Lys Glu His Gly Lys Tyr Thr Ala
        35                  40                  45

Asp Leu Glu Asp Gly Gly Tyr Thr Ile Asn Ile Arg Phe Ala Gly
    50                  55                  60

<210> SEQ ID NO 3
<211> LENGTH: 63
<212> TYPE: PRT
<213> ORGANISM: Artificial
<220> FEATURE:
<223> OTHER INFORMATION: PpL mutant

<400> SEQUENCE: 3

Glu Gln Val Thr Ile Lys Glu Asn Ile Tyr Phe Glu Asp Gly Thr Val
1               5                   10                  15

Gln His Ala Thr Phe Lys Gly Thr Phe Ala Glu Ala Thr Ala Glu Ala
            20                  25                  30

Tyr Arg Tyr Ala Asp Leu Leu Ser Lys Glu His Gly Lys Tyr Thr Ala
        35                  40                  45

Asp Leu Glu Asp Gly Gly Tyr Thr Ile Asn Ile Arg Phe Ala Gly
    50                  55                  60
```